United States Patent [19]

Edwards et al.

[11] Patent Number: 5,158,877
[45] Date of Patent: Oct. 27, 1992

[54] GENE SYNTHESIS

[75] Inventors: Richad M. Edwards, Thame; Sally E. Adams, Kidlington, both of England

[73] Assignee: British Bio-Technology Limited, Oxford, England

[21] Appl. No.: 582,926

[22] PCT Filed: Apr. 14, 1989

[86] PCT No.: PCT/GB89/00384

§ 371 Date: Oct. 11, 1990

§ 102(e) Date: Oct. 11, 1990

[87] PCT Pub. No.: WO89/09824

PCT Pub. Date: Oct. 19, 1989

[30] Foreign Application Priority Data

Apr. 15, 1988 [GB] United Kingdom ............... 8808892

[51] Int. Cl.$^5$ ................... C12P 19/34; C07H 15/12; C07H 17/00
[52] U.S. Cl. ................... 435/91; 435/172.3; 435/320.1; 435/172.1; 536/27; 935/11; 935/6; 935/18; 935/10
[58] Field of Search ............ 435/91, 320.1, 172.3, 435/172.1; 536/27; 935/11, 6, 18, 10

[56] References Cited

U.S. PATENT DOCUMENTS 4,657,858 4/1987 Davison, Jr. .................. 435/69.1

FOREIGN PATENT DOCUMENTS 0253193 1/1988 European Pat. Off. .

OTHER PUBLICATIONS

Narang et al. 1987 Biochem. Biophys. Res. Commun. 134,407–411.
Rink et al. 1984, Nucleic Acids Res. 12, 6369–6387.
Balland et al. 1985, Biochimie, 67,725–736.
Aldovini et al 1986, Proc. Nat'l. Acad. Sci USA 83,6672–6676.
Arya et al. 1985, *Trans-Activator Gene of Human T-Lymphotropic Virus Type III* (HTLV-III), in: Kulstad. R (ed.) 1986, *Aids:Papers from Science, 1982-1985,* American Soc. Adv. Sci. Washington, D.C., pp. 553–563.
Arentzen et al. 1984, Nuc. Acids Res. 12, 777–787.
Roberts, R. J. 1987, Nuc. Acids Res. 15 (Suppl.), pp. 189–217.
Ratner et al. 1985 Nature 313, 277–284.

*Primary Examiner*—Robert A. Wax
*Assistant Examiner*—Christopher G. F. Low
*Attorney, Agent, or Firm*—Allegretti & Witcoff, Ltd.

[57] ABSTRACT

Double stranded DNA (ds-DNA) can be prepared by preparing a hybrid DNA containing a single stranded portion and a double stranded portion and carrying out in vivo gap repair on the hybrid DNA. The hybrid DNA is prepared by synthesizing a single strand of DNA and introducing the single strand into double stranded DNA. This method of synthesis can be used to make synthetic genes, including synthetic DNA coding for the TAT protein of HIV-I, and incorporates useful restriction sites. Also included are flanking restriction sites to simplify the incorporation of the gene into any desired expression system.

7 Claims, 5 Drawing Sheets

FIG. 1

TAT cDNA SEQUENCE.

```
    M   E   P   V   D   P   R   L   E   P   W   K   H   P   G   S   Q   P   K   T
    ATGGAGCCAGTAGATCCTAGACTAGAGCCCTGGAAGCATCCAGGAAGTCAGCCTAAAACT
                10          20          30          40          50          60

A   C   T   N   C   Y   C   K   K   C   C   F   H   C   Q   V   C   F   I   T
    GCTTGTACCAATTGCTATTGTAAAAAGTGTTGCTTTCATTGCCAAGTTTGTTTCATAACA
                70          80          90         100         110         120

K   A   L   G   I   S   Y   G   R   K   K   R   R   Q   R   R   R   P   P   Q
    AAAGCCTTAGGCATCTCCTATGGCAGGAAGAAGCGGAGACAGCGACGAAGACCTCCTCAA
               130         140         150         160         170         180

G   S   Q   T   H   Q   V   S   L   S   K   Q   P   T   S   Q   S   R   G   D
    GGGCAGTCAGACTCATCAAGTTTCTCTATCAAAGcaaCCACCTCCCAATCCCGAGGGGAC
               190         200         210         220         230         240

P   T   G   P   K   E   *
    CCGACAGGCCCGAAGGAATAG
               250         260
```

Splice site indicated in lower case

FIG. 2   SEQUENCE OF SYNTHETIC TAT GENE AND LOCATION OF USEFUL RESTRICTION SITES.

```
            M   E   P   V   D   P   R   L   E   P   W   K   H   P   G   S
         AAGCTTACCTGCCATGGAACCAGTCGACCCTAGACTGGAACCGTGGAAACACCCGGGTTC
         HinDIII BspMI NcoI         SalI                         SmaI
            10          20          30          40          50          60

Q   P   K   T   A   C   T   N   C   Y   C   K   K   C   C   F   H   C   Q   V
         CCAGCCGAAAACTGCATGCACCAACTGTTACTGTAAAAAGTGTTGCTTCCACTGTCAAGT
                            SphI
            70          80          90         100         110         120

C   F   I   T   K   A   L   G   I   S   Y   G   R   K   K   R   R   Q   R   R
         TTGTTTCATCACCAAGGCTTTGGGTATCTCCTACGGTCGTAAGAAACGTAGACAGGCCAG
                        BstXI
           130         140         150         160         170         180

R   P   P   Q   G   S   Q   T   H   Q   V   S   L   S   K   Q   P   T   S   Q
         ACGTCCACCGCAAGGTTCTCAGACTCATCAAGTTTCCTTGTCCAAGCAACCGACCTCCCA
         AatII
           190         200         210         220         230         240

S   R   G   D   P   T   G   P   K   E   *   *
         ATCTCGCGGTGACCCGACAGGTCCTAAGGAATAGTAAGGATCCGAATTC
         BstEII            MstII                BamHI EcoRI
           250         260         270         280
```

FIG. 3a    DESIGN OF OLIGOMERS FOR SYNTHETIC TAT GENE.

```
BBG512           M   E   P   V   D   P   R   L   E   P   W   K   H   P   G   S
       a AGCTTACCTGCCATGGAACCAGTCGAACCTGACCCCTAGACTGGAACCCGTGGAAACACCCGGGTTC
         HinDIII|BspMI|NcoI                SalI                        SmaI
         ttcga ATGGACGGTAC-BBG514
                10            20            30            40            50            60

Q   P   K   T   A   C   T   N   C   Y   C   K   K   C   C   F   H   C   Q   V
         CCAGCCGAAAACTGCATGCACCAACTGTTACTGTAAAAAGTGTTGCTTCCACTGTCAAGT
                     SphI
                70            80            90           100           110           120

C   F   I   T   K   A   L   G   I   S   Y   G   R   K   K   R   Q   R   R
         TTGTTTCATCACCAAGGCTTTGGGTATCTCCTACGGTCGTAAGAAACGTAGACAGGGCAG
                     BstXI|||||||||
                           GAAACCCATAGAGGAT-BBG511
               130           140           150           160           170           180

S   R   G   D   P   T   G   P   K   E   *    BBG513
                                                                              *
                                                                              |
                                                                              |
          R   P   P   Q   G   S   Q   T   H   Q   V   S   L   S   K   Q   P   T   S   Q
         ACGTCCACCGGCAAGGTTCTCAGACTCATCAAGTTTCCTTGTCCAAGCAACCGACCTCCCA
         AatII                       MstII
               190           200           210           220           230           240

S   R   G   D   P   T   G   P   K   E   *    BBG513
         ATCTCGGCGGTGACCCGACAGGTCCTAAGGAATAGTAAGGATCCG aattc
         BstEII                                       |||BamHI|EcoRI
                                    BBG515-ATTCCTAGGCTTAA g
               250           260           270           280
```

FIG. 3b

SUMMARY OF USEFUL RESTRICTION SITES.

| ENZYME | SEQUENCE | POSITION |
|---|---|---|
| HinDIII | AAGCTT | 1 |
| BspMI | ACCTGC | 7 |
| NcoI | CCATGG | 12 |
| SalI | GTCGAC | 23 |
| SmaI | CCCGGG | 52 |
| SphI | GCATGC | 74 |
| BstXI | CCAAGGCTTTGG | 132 |
| AatII | GACGTC | 180 |
| BstEII | GGTGACC | 248 |
| MstII | CCTAAGG | 263 |
| BamHI | GGATCC | 278 |
| EcoRI | GAATTC | 284 |

SUMMARY OF ASSEMBLY PROCEDURE.

GENE SYNTHESIS

This invention relates to a method of synthesising double stranded DNA (ds-DNA), and to ds-DNA produced by such a method. ds-DNAs produceable by a method in accordance with the invention include synthetic genes coding for the transactivator of human immunodeficiency virus, to which the invention also relates.

Examples of ds-DNA and in particular total gene synthesis are becoming increasingly common as the reliability of oligonucleotide synthesis and the efficiency of assembly methods continue to improve. Gene synthesis is now an invaluable tool for the molecular biologist because of the total control it affords over restriction sites, codon usage and subsequent genetic manipulation and expression of the gene. This is particularly true where the gene is refractory to manipulation because of a lack of useful restriction sites or because it is derived from a spliced RNA, as is true in the case of the transactivator (TAT) protein of HIV1.

Methods of oligonucleotide synthesis have been reviewed extensively elsewhere (Gait, M. J. (1984) In M. J. Gait (ed), *Oligonucleotide Synthesis: a Practical Approach*, IRL Press, Oxford pp. 1-22). A number of different methods for the assembly of oligonucleotides have been described which divide into two main groups. In the first pioneered by Khorana and co-workers (Khorana, H. G. (1979) *Science* 203, 614-625), both strands of the desired sequence are divided such that adjacent pairs of complementary oligomers possess short (4-7 base) cohesive ends. The oligomers are then synthesised, kinased and annealed in pairs prior to ligation in a duplex corresponding to the intact gene. The ends of the gene are also endowed with cohesive ends to allow subsequent cloning of the gene in an appropriate vector. A recent development has been the successful solid phase assembly of a gene for cow colostrum trypsin inhibitor (Hostomsky, Z., Smrt, J., Arnold, L., Tocik, Z. and Paces, V. (1987) *Nucelic Acids Research* 15, 489-4856). The essential feature of these approaches is that both strands of the duplex are synthesised in their entirety.

The second strategy is based on the use of longer oligomers that share a complementary 3, end (Rossi, J. J., Kierzek, R., Huang, T., Walker, P. A. and Itakura, K. (1982) *J. Biol. Chem.* 257, 9226). Annealing a pair of such oligomers results in a short duplex region with two long single stranded extensions. Treating this partial duplex with Klenow fragment of DNA polymerase I in the presence of all four dNTP's results in the conversion of this structure to a complete duplex with blunt ends. This method has been successfully applied to the synthesis of a gene for Eglin C (Rink, H., Liersch, M., Sieber, P. and Meyer, F. (*1984*) *Nucleic Acids Research* 12, 6369-6387) and could in theory be extended to the construction of larger genes. It is attractive in that it reduces the amount of oligonucleotide synthesis required, but it has its drawbacks in that rearrangements and deletions are not uncommon.

A method of synthesising lengths of ds-DNA, particularly synthetic genes, has now been developed which reduces the amount of oligonucleotide synthesis required in the Khorana method but which does not have all the drawbacks of the Klenow fragment method.

According to a first aspect of the invention, there is provided a method of synthesising double stranded DNA, the method comprising preparing hybrid DNA containing a single stranded portion and a double stranded portion and carrying out in vivo gap repair on the hybrid DNA.

The single stranded portion may comprise at least 10, 20, 50 or 100 nucleotides.

The hybrid DNA (which may be a vector such as a plasmid) may be prepared by synthesising a single strand of DNA and introducing the single strand into double stranded DNA.

The single strand can conveniently be provided with double stranded ends and subsequently introduced into a double stranded vector. The double stranded ends of the single strand may be sticky, to correspond with restriction endonuclease cuts (natural or synthesised) in the ds-DNA, and will therefore for preference be different from one another. If a standard pair of sticky ends is used (for example HindIII and EcoRI), a "cassette" system is developed, whereby cassettes of various ss-DNAs can be inserted into, for example, a common vector system.

The hybrid DNA may comprise at least two single stranded regions, the or each of the single stranded regions being separated by double stranded DNA. This embodiment has two advantages. First, the ds-DNA separator is useful in that it can be used as a sequencing primer. Secondly, the ds-DNA separator can form a means to link two separately synthesised ss-DNAs together if it is not feasible or convenient to synthesise the two as one.

Preferred ds-DNA synthesised by a method in accordance with the first aspect of the invention includes a number of genes, particularly the tat gene of the Human Immunodeficiency Virus which encodes the transactivator TAT.

In addition to the three principle structural genes gag, pol and env the Human Immunodeficiency Virus (HIV1) possesses a number of shorter open readinig frames with less well defined functions. The tat gene is composed of two exons and encodes the transactivator TAT, a regulatory protein involved in the activation of the HIV long terminal repeat (LTR). TAT is believed to exert its major effect on HIV gene expression by acting as an anti-terminator. Recent studies suggest that TAT interacts with a site in the transcribed R region of the LTR to prevent the premature termination of the RNA before it reaches the viral genes. Thus transcription beyond base 59 of the LTR derived transcript occurs only in the presence of TAT. The site at which TAT acts has been defined by deletion analysis and is known as TAR (for trans-acting response element). It is not yet known whether TAT exerts its effect via the genomic TAR or an mRNA structural motif encoded by TAR but it is becoming clear that regulation of expression from the 5' LTR involves the interaction of a number of other transcription factors in addition to TAT.

The complete nucleotide sequence of a number of HIV strains have been described. The deduced protein sequence for TAT we have used in the design of a synthetic TAT gene was taken from the first published sequence (Ratner et al. *Nature* 313, 277-284 (1985)).

The function of TAT as an anti-terminator has been established more recently (Wright et al. *Science* 234, 988-992 (1986), Kao et al. *Nature* 330, 489-493 (1987)).

The construction of a synthetic gene encoding TAT is not described in any of the above documents.

In order to facilitate the the further delineation of the mode of trans-activation by TAT, the use of TAT and TAR in the construction of inducible expression systems and the production of TAT protein for structural and immunological studies an improved novel synthetic modular gene for TAT is sought.

It is by no means easy to predict the design of an improved gene for TAT, since the factors that determine the expressibility of a given DNA sequence are still poorly understood. Furthermore, the utility of the gene in various applications will be influenced by such considerations as codon usage and restriction sites. The present invention relates to synthetic TAT genes which are distinct from the natural TAT gene and have advantages in the ease with which they can be modified due to the presence of useful restriction sites.

According to a second aspect of the invention, there is provided DNA coding for TAT and having restriction sites for the following enzymes:

HinDIII, BspMI, NcoI, SalI, SmaI, SphI, BstXI,

AatII, BstEII, MstII, BamHI and EcoRI.

According to a third aspect of the invention, there is provided DNA including the following sequence:

```
A   AGC  TTA  CCT  GCC  ATG  GAA  CCA  GTC  GAC  CCT  AGA  CTG
GAA CCG  TGG  AAA  CAC  CCG  GGT  TCC  CAG  CCG  AAA  ACT
GCA TGC  ACC  AAC  TGT  TAC  TGT  AAA  AAG  TGT  TGC  TTC
CAC TGT  CAA  GTT  TGT  TTC  ATC  ACC  AAG  GCT  TTG  GGT
ATC TCC  TAC  GGT  CGT  AAG  AAA  CGT  AGA  CAG  CGC  AGA
CGT CCA  CCG  CAA  GGT  TCT  CAG  ACT  CAT  CAA  GTT  TCC
TTG TCC  AAG  CAA  CCG  ACC  TCC  CAA  TCT  CGC  GGT  GAC
CCG ACA  GGT  CCT  AAG  GAA  TAG  TAA  GGA  TCC  GAA  TTC
```

The design for the synthetic tat genes was based on the amino acid sequence deduced from the published cDNA sequence (see FIG. 1). It was found possible to assign appropriate codons to the synthetic gene aiming for a compromise between E. coli and yeast codon bias. For the codons where no compromise choice was available a strategy of alternating the codon choice was devised such that runs of sub-optimal codons for one organism were avoided. In addition a number of restriction sites were built into the sequence to facilitate subsequent manipulation of segments of the tat gene. For the preferred sequence, the codon selection was then randomised within this set of constraints by computer and the sequence checked finally to ensure that there were no regions of extensive direct or inverted repeats. To simplify the incoporation of the tat gene into expression vectors a number of flanking restriction sites were chosen including an upstream HinDIII site and downstream BamHI and EcoRI sites. Provision was also made for the construction of tat fusion derivatives with or without the initiator methionine through the inclusion of NcoI and BsoMI sites that encompass the initiator ATG. These sites allow the retention of a reasonable Kozak sequence that may be important for applications involving the expression of the synthetic gene in mammalian cells.

Synthetic genes in accordance with the invention are designed primarily for expression in yeast and E. coli but we would expect them to be capable of expression in other systems including mammalian and insect cells.

According to a fourth aspect of the invention, there is provided a genetic construct comprising DNA according to the first or second aspect or a fragment thereof. The fragment may comprise at least 10, 20, 30, 40 or 50 nucleotides. A genetic construct in accordance with the third aspect may be a vector, such as a plasmid, cosmid or phage.

According to a fifth aspect of the invention, there is provided a process for the preparation of DNA in accordance with the second or third aspect or a genetic construct in accordance with the fourth aspect, the process comprising coupling successive nucleotides and/or ligating appropriate oligomers. It is preferred, however, that a method in accordance with the first aspect be used.

The invention also relates to other nucleic acid (including RNA) either corresponding to or complementary to DNA in accordance with the second or third aspects.

Preferred embodiments and examples of the invention will now be described. In the following description, reference is made to a number of drawings, in which:

FIG. 1 shows the cDNA sequence for TAT together with the deduced amino acid sequence;

FIG. 2 shows the sequence of a preferred synthetic gene for TAT along with location of useful restriction sites;

Figure 4:
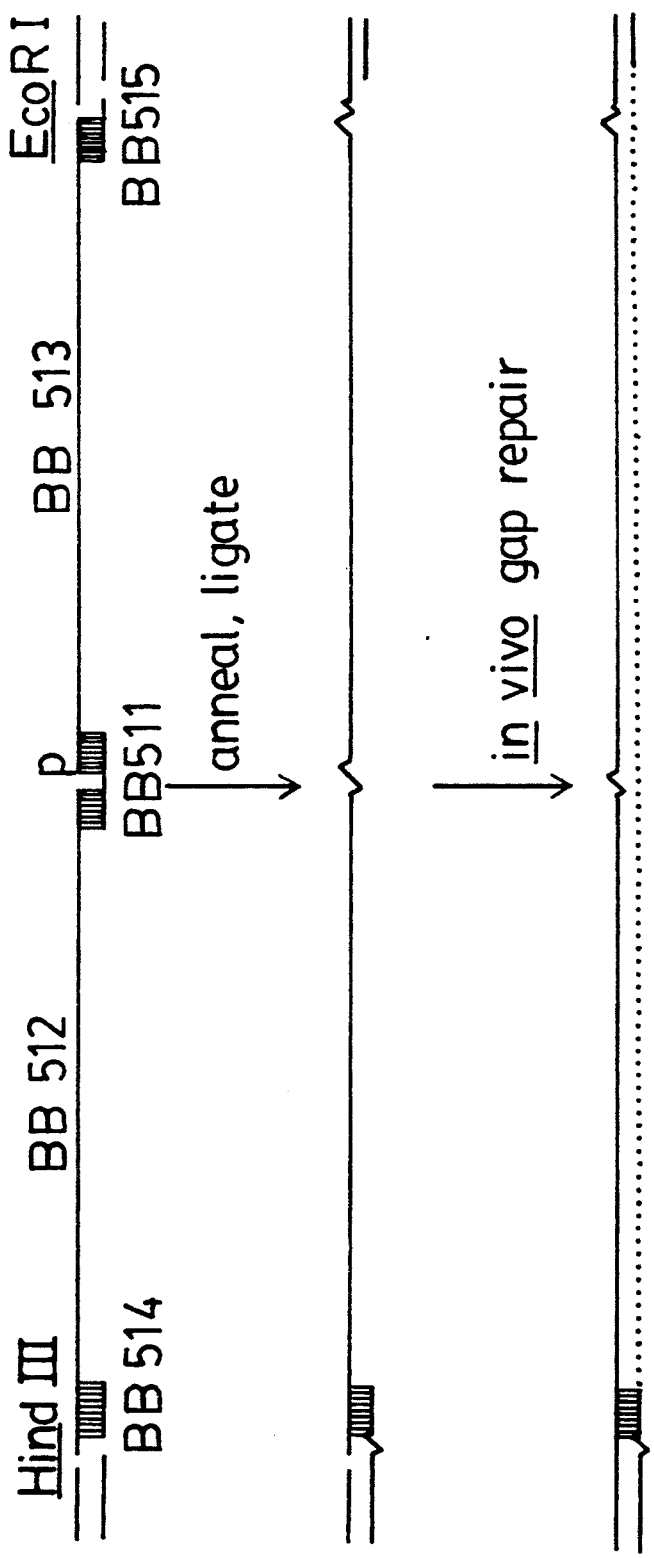

FIG. 3A-B shows the sequence of the TAT synthetic gene divided into oligonucleotides; and FIG. 4 shows a summary of the assembly procedure used.

CONSTRUCTION OF THE GENE

The top strand of the desired gene sequence was divided into 2 large oligodeoxyribonucleotides (oligomers) BB512 and BB513 as depicted in FIG. 3. The ligation of these two large oligomers and their subsequent cloning into the plasmid vector pUC18 was then accomplished through the use of small complementary bridging oligomers. BB511 is a 16mer that is complementary to the 3' 8 bases of BB512 and the 5' 8 bases of BB513. BB514 is an 11mer that serves as an adapter by annealing to the 5'end of BB512 in such a way as to leave a four base HindIII compatible cohesive end. Similarly, BB515 is a 14mer that anneals to the 3' end of BB513 to provide an EcoRI cohesive end.

The oligomers were synthesised by automated solid phase phophoramidite chemistry. Following de-blocking and removal from the controlled pore glass support the oligomers were purified on denaturing polyacrylamide gels, further purified by ethanol precipitation and finally dissolved in water prior to estimation of their concentration.

To minimise the possibility of mis-ligation only BB513, the 3' of the two large oligomers, was kinased. All five oligomers were annealed with the three small adapter and bridging oligomers in two fold molar excess. The annealed mixture was then ligated directly to EcoRI/HinDIII cut DNA of the plasmid vector pUC18. This procedure allows the sense strand of tat to be ligated into the vector resulting in plasmid DNA carrying a single stranded gap covering the tat gene.

This procedure relies on in vivo gap repair to fill in the single stranded region. The ligated product was transformed into HW87 and plated on L-agar plates containing 100 mcg.ml$^{-1}$ ampicillin. Colonies containing potential clones were then grown up in L-broth containing ampicillin at 100 mcg.ml$^{-1}$ and plasmid DNA isolated. Positive clones were identified by direct dideoxy sequence analysis of the plasmid DNA using the 17 base universal primer, a reverse sequencing primer complementary to pUC18 on the other side of the polylinker region. Some of the oligomers employed in the assembly of the gene were also used as internal sequencing primers. One tat clone was subsequently re-sequenced on both strands to confirm that no mutations were present.

METHODS

All the basic techniques of genetic manipulation used in the manufacture of this gene are well known to those skilled in the art of genetic engineering. A description of most of the techniques can be found in one of the following laboratory manuals: Molecular Cloning by T. Maniatis, E. F. Fritsch and J. Sambrook published by Cold Spring Harbor Laboratory, Box 100, New York, or Basic Methods in Molecular Biology by L. G. Davis, M. D. Dibner and J. F. Battey published by Elsevier Science Publishing Co. Inc. New York.

Additional and modified methodologies are detailed below.

1) Oligonucleotide Synthesis

The oligonucleotides were synthesised by automated phosphoramidite chemistry using cyanoethyl phosphoramidtes. The methodology is now widely used and has been described (Beaucage, S. L. and Caruthers, M. H. *Tetrahedron Letters* 24, 245 (1981)).

2) Purification of Oligonucleotides

The oligonucleotides were de-protected and removed from the CPG support by incubation in concentrated NH$_3$. Typically, 50 mg of CPG carrying 1 micromole of oligonucleotide was de-protected by incubation for 5 hr at 70° in 600 mcl of concentrated NH$_3$. The supernatant was transferred to a fresh tube and the oligomer precipitated with 3 volumes of ethanol. Following centrifugation the pellet was dried and resuspended in 1 ml of water. The concentration of crude oligomer was then determined by measuring the absorbance at 260 nm.

For gel purification 10 absorbance units of the crude oligonucleotide were dried down and resuspended in 15 mcl of marker dye (90% de-ionised formamide, 10 mM tris, 10 mM borate, 1 mM EDTA, 0.1% bromophenol blue). The samples were heated at 90° for 1 minute and then loaded onto a 1.2 mm thick denaturing polyacrylamide gel with 1.6 mm wide slots. The gel was prepared from a stock of 15% acrylamide, 0.6% bisacrylamide and 7M urea in 1× TBE and was polymerised with 0.1% ammonium persulphate and 0.025% TEMED. The gel was pre-run for 1 hr. The samples were run at 1500 V for 4-5 hr. The bands were visualised by UV shadowing and those corresponding to the full length product cut out and transferred to micro-testubes. The oligomers were eluted from the gel slice by soaking in AGEB (0.5 M ammonium acetate, 0.01 M magnesium acetate and 0.1% SDS) overnight. The AGEB buffer was then transferred to fresh tubes and the oligomer precipitated with three volumes of ethanol at −70° for 15 min. The precipitate was collected by centrifugation in an Eppendorf microfuge for 10 min, the pellet washed in 80% ethanol, the purified oligomer dried, redissolved in 1 ml of water and finally filtered through a 0.45 micron micro-filter. The concentration of purified product was measured by determining its absorbance at 260 nm.

3) Kinasing of Oligomers 250 pmole of BB513 was dried down and resuspended in 20 mcl kinase buffer (70 mM Tris pH 7.6, 10 mM MgCl$_2$, 1 mM ATP, 0.2 mM spermidine, 0.5 mM dithiothreitol). 10 u of T4 polynucleotide kinase was added and the mixture incubated at 37° for 30 min. The kinase was then inactivated by heating at 85° for 15 min.

4) Annealing 10 pmol of BB512 and BB513 were mixed with 20 pmol each of oligomers BB511, BB514 and BB515. The mixture was heated to 90° for 10 minutes and then cooled slowly to room temperature to allow the oligomers to anneal.

5) Ligation

The annealed oligomers were then mixed with 10 X ligase buffer to give a final ligase reaction mixture (50 mM Tris pH 7.5, 10 mM MgCl$_2$, 20 mM dithiothreitol, 1 mM ATP. T4 DNA ligase was added at a rate of 100 u per 50 mcl reaction and ligation carried out at 15° for 4 hr.

6) Cloning of Fragment 0.5 mcg of pUC18 DNA was prepared by cleavage with HinDIII and BamHI as advised by the suppliers. The digested DNA was run on an 0.8% LGT gel and the vector band purified as described below.

20 ng of cut vector DNA was then ligated to various quantities of annealed tat DNA ranging from 2 to 20 ng for 4 hr using the ligation buffer described above. The ligation products were used to transform competent HW87 as has been described. Ampicillin resistant transformants were selected on L-agar plates containing 100 mcg.ml$^{-1}$ ampicillin.

7) Agarose Gel Electrophoresis

The digested vector DNA was purified on a 0.8% low gelling temperature agarose gel in 1× TBE buffer (0.094 M Tris pH8.3, 0.089 M boric acid, 0.25 mM EDTA) containing 0.5 mcg.ml$^{-1}$ ethidium bromide. The band corresponding to linearised plasmid DNA was excised and the DNA extracted as below.

8) Isolation of Vector DNA

The volume of the gel slice was estimated from its weight and then melted by incubation at 65° for 10 min. The volume of the slice was then made up to 400 ul with TE (10 mM Tris pH 8.0, 1 mM EDTA) and Na acetate added to a final concentration of 0.3 M. 10 mcg of yeast tRNA was also added as a carrier. The DNA was then subjected to three rounds of extraction with equal volumes of TE equilibrated phenol followed by three extractions with ether that had been saturated with water. The DNA was precipitated with 2 volumes of ethanol, centrifuged for 10 min in a microfuge, the pellet washed in 70% ethanol and finally dried down. The DNA was taken up in 20 mcl of TE and 2 mcl run on a 1% agarose gel to estimate the recovery of DNA.

9) Isolation of Plasmid DNA

Plasmid DNA was prepared from the colonies containing potential tat clones essentially as described (Ish-Horowicz, D., Burke, J. F. *Nucleic Acids Research* 9 2989-2998 (1981).

10) Dideoxy Sequencing

The protocol used was essentially as has been described (Biggin, M. D., Gibson, T. J., Hong, G. F. *P.N.A.S.* 80 3963-3965 (1983)). The method was modified to allow sequencing on plasmid DNA as described (Guo, L-H., Wu, R. *Nucleic Acids Research* 11 5521-5540 (1983).

11) Transformation

Transformation was accomplished using standard procedures. The strain used as a recipient in the cloning was HW87 which has the following genotype:

araD139(ara—leu)del7697 (lacIPOZY)del74 galU galK hsdR rpsL srl recA56

Any other standard cloning recipient such as HB101 would be adequate.

We claim:

1. A method of synthesising double stranded DNA, the method comprising preparing hybrid DNA coding for the TAT protein of HIV-I as shown in FIG. 1 containing a single stranded portion and a double stranded portion and carrying out in vivo gap repair on the hybrid DNA.

2. A method as claimed in claim 1, wherein the hybrid DNA is prepared by synthesising a single strand of DNA and introducing the single strand into double stranded DNA.

3. A method as claimed in claim 1 or 2, wherein the hybrid DNA is a vector.

4. A method as claimed in claim 2, wherein the single strand is provided with double stranded ends and subsequently introduced into a double stranded vector.

5. A method as claimed in claim 4, wherein the double stranded ends of the single strand are sticky.

6. A method as claimed in any one of claims 1 to 5, wherein the hybrid DNA comprises at least two single stranded regions, the or each of the single stranded regions being separated by double stranded DNA.

7. A synthetic DNA coding for the TAT protein of HIV-I which consists essentially of the sequence:

```
A   AGC TTA CCT GCC ATG GAA CCA GTC GAC CCT AGA CTG
GGA CCG TGG AAA CAC CCG GGT TCC CAG CCG AAA ACT
GCA TGC ACC AAC TGT TAC TGT AAA AAG TGT TGC TTC
CAC TGT CAA GTT TGT TTC ATC ACC AAG GCT TTG GGT
ATC TCC TAC GGT CGT AAG AAA CGT AGA CAG CGC AGA
CGT CCA CCG CAA GGT TCT CAG ACT CAT CAA GTT TCC
TTG TCC AAG CAA CCG ACC TCC CAA TCT CGC GGT GAC
CCG ACA GGT CCT AAG GAA TAG TAA GGA TCC GAA TTC.
```

\* \* \* \* \*